United States Patent [19]

Glamkowski et al.

[11] Patent Number: 4,623,657
[45] Date of Patent: Nov. 18, 1986

[54] SPIRO [BENZOFURAN-2(3H),1'-CYCLOHEPTANE]S AND THEIR THERAPEUTIC USE

[75] Inventors: Edward J. Glamkowski, Warren; Frederick J. Ehrgott, Jr., Piscataway, both of N.J.

[73] Assignee: Hoechst-Roussel Pharmaceuticals Inc., Somerville, N.J.

[21] Appl. No.: 772,974

[22] Filed: Sep. 5, 1985

[51] Int. Cl.$^4$ .............. A61K 31/34; C07D 307/94
[52] U.S. Cl. ................................ 514/462; 549/345
[58] Field of Search .................... 549/345; 514/462

[56] References Cited

U.S. PATENT DOCUMENTS 4,404,221 9/1983 Glamkowski et al. ............ 549/345
4,517,311 5/1985 Glamkowski et al. ............ 549/345

Primary Examiner—Henry R. Jiles
Assistant Examiner—Bernard I. Dentz
Attorney, Agent, or Firm—Tatsuya Ikeda

[57] ABSTRACT

There are described compounds of the formula

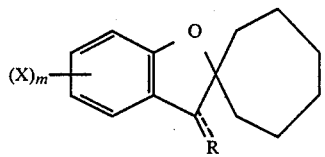

where each X is independently H, halogen, loweralkyl, loweralkoxy or OH; m is 1 or 2; and R is —H, =O,

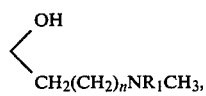

$=CH(CH_2)_nNR_1CH_3$, $—CH_2(CH_2)_nNR_1R_2$,
$=N—OH$, $=N—OCH_2(CH_2)_nNR_1R_3$,

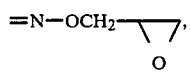

$=N—OCH_2CHOHCH_2NR_1R_3$, $—NR_2R_3$, $—OH$ or $—OCH_2(CH_2)_nNR_1R_2$, n being 1 or 2, $R_1$ being loweralkyl, $R_2$ being H, loweralkyl, loweralkanoyl, arylloweralkyl, arylloweralkanoyl, diarylloweralkyl, diarylloweralkanoyl, $—CO_2C_2H_5$ or $—CN$, and $R_3$ being H, loweralkyl, arylloweralkyl or diarylloweralkyl, or a pharmaceutically acceptable acid addition salt thereof, which are useful as antihypertensive, anticonvulsant, analgesic and antidepressant agents.

50 Claims, No Drawings

SPIRO [BENZOFURAN-2(3H),1'-CYCLOHEPTANE]S AND THEIR THERAPEUTIC USE

This invention relates to novel compounds of the formula,

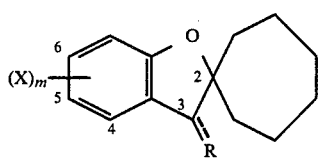

(I)

where each X is independently H, halogen, loweralkyl, loweralkoxy or OH; m is 1 or 2; and R is —H, =O,

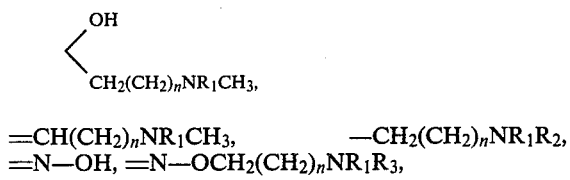

=CH(CH$_2$)$_n$NR$_1$CH$_3$, —CH$_2$(CH$_2$)$_n$NR$_1$R$_2$, =N—OH, =N—OCH$_2$(CH$_2$)$_n$NR$_1$R$_3$,

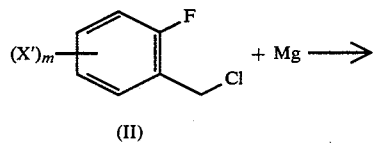

=N—OCH$_2$CHOHCH$_2$NR$_1$R$_3$, —NR$_2$R$_3$, —OH or —OCH$_2$(CH$_2$)$_n$NR$_1$R$_2$, n being 1 or 2, R$_1$ being loweralkyl, R$_2$ being H, loweralkyl, loweralkanoyl, arylloweralkyl, arylloweralkanoyl, diarylloweralkyl, diarylloweralkanoyl, —CO$_2$C$_2$H$_5$ or —CN, and R$_3$ being H, loweralkyl, arylloweralkyl or diarylloweralkyl, or a pharmaceutically acceptable acid addition salt thereof, which are useful as antihypertensive, anticonvulsant, analgesic and antidepressant agents; to pharmaceutical compounds comprising same; and to methods of treating patients in need of relief from high blood pressure, convulsion, pain or depression with said pharmaceutical compositions.

Throughout the specification and the appended claims, a given chemical formula or name shall encompass all stereo, optical, and geometrical isomers thereof where such isomers exist, as well as pharmaceutically acceptable acid addition salts thereof and solvates thereof such as for instance hydrates.

The following general rules of terminology shall apply throughout the specification and the appended claims.

Unless otherwise stated or indicated, the term loweralkyl denotes a straight or branched alkyl group having from 1 to 6 carbon atoms. Examples of said loweralkyl group include methyl, ethyl, n-propyl, iso-propyl, n-butyl, iso-butyl, sec-butyl, t-butyl and straight- and branched-chain pentyl and hexyl.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term halogen shall mean fluorine, chlorine, bromine or iodine.

Unless otherwise stated or indicated, the term aryl shall mean a phenyl group having 0, 1, 2 or 3 substituents each of which being independently loweralkyl, loweralkoxy, halogen or CF$_3$, and the term diaryl shall mean two such aryl groups each of which being independent of the other.

The term loweralkanoyl shall mean a group obtained by removing a hydroxy group from the carboxyl group of a loweralkanoic acid, and thus it includes for instance formyl, acetyl and the like.

The term arylloweralkanoyl shall mean a loweralkanoyl group having an aryl substituent thereon, the terms loweralkanoyl and aryl having the respective meanings defined above.

The compounds of this invention are prepared by following one or more of the steps described below. Throughout the description of the synthetic steps, the definitions of X, m, R, R$_1$, R$_2$, R$_3$ and n are as given above unless otherwise stated or indicated, and X' appearing below shall mean H, halogen, loweralkyl or loweralkoxy, R$_4$ appearing below shall mean loweralkyl, arylloweralkyl or diarylloweralkyl and R$_5$CO appearing below shall mean loweralkanoyl, arylloweralkanoyl or diarylloweralkanoyl unless specifically stated or indicated otherwise.

STEP A

A compound of formula II where X' is H, halogen, loweralkyl or loweralkoxy is reacted with magnesium to prepare the corresponding Grignard reagent and the latter is reacted with cycloheptanone to obtain (after hydrolysis) a compound of formula III.

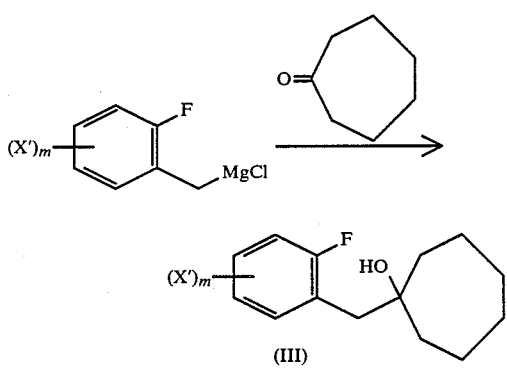

The first step is typically conducted in a suitable anhydrous medium such as diethyl ether in the vicinity of room temperature. The second step is also typically conducted in a suitable anhydrous medium such as diethyl ether in the vicinity of room temperature.

Compounds of formula III which are useful as an intermediate for synthesizing other compounds of this invention are believed to be novel.

STEP B

Compound III is cyclized in the presence of a strong base such as sodium or potassium hydride to afford a compound of formula IV.

(III) + NaH ⟶ 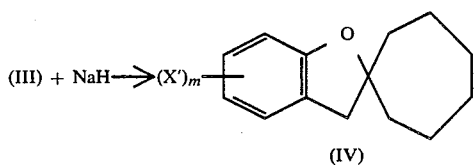

Said cyclization is typically conducted in a suitable anhydrous medium such as dimethylformamide, benzene, or a mixture of benzene and dimethylformamide under a reflux condition.

STEP C

Compound IV is oxidized to a ketone of formula V with a suitable oxidizing agent such as potassium persulfate plus cupric sulfate.

(IV) $\xrightarrow{K_2S_2O_8}$ 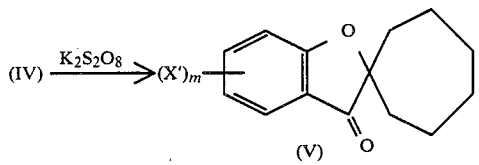

Said oxidation is typically conducted in a suitable medium such as a mixture of water and acetonitrile under a reflux condition. It is desirable that the molar amount of potassium persulfate be in excess of compound IV and that the molar amount of cupric sulfate be substantial, for instance, equimolar with respect to compound IV.

STEP D

A compound of the formula $ClCH_2(CH_2)_nNR_1CH_3$ is reacted with magnesium to prepare the corresponding Grignard reagent and the latter is reacted with compound V to afford (after hydrolysis) a compound of formula VI.

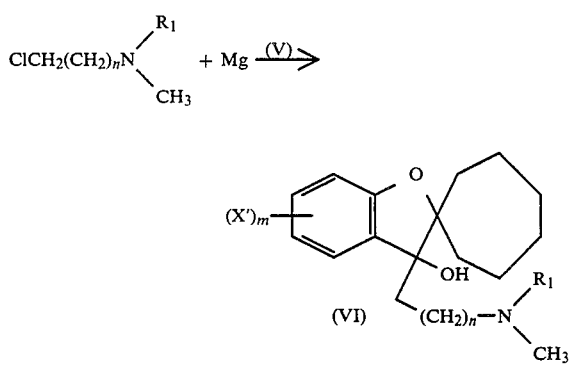

The first step is typically conducted in a suitable anhydrous medium such as tetrahydrofuran or a mixture of ether and benzene under a reflux condition. The second step is also conducted typically in a suitable anhydrous medium such as tetrahydrofuran or a mixture of ether and benzene under a reflux condition.

STEP E

Compound VI is converted to a compound of formula VII by dehydration.

(VI) ⟶ 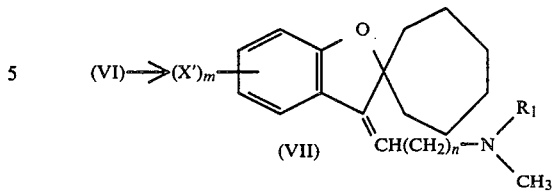

Said dehydration is typically conducted in a suitable solvent such as ethanol and in the presence of a suitable acid such as hydrochloric acid in the vicinity of room temperature, or preferably at the reflux temperature of the mixture.

STEP F

Compound VII is reduced to a compound of formula VIII.

(VII) + $H_2$ ⟶ 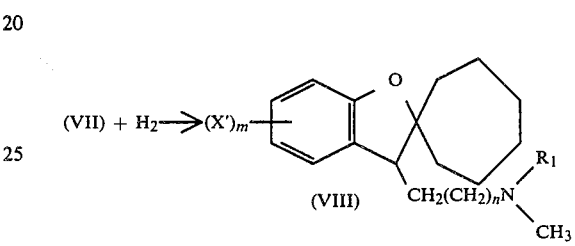

Said reduction is typically conducted with the aid of a suitable catalyst such as palladium or 1% platinum on carbon in a suitable medium such as ethanol/water (95:5) under a hydrogen gas pressure of a few atmospheres or less and in the vicinity of room temperature.

STEP G

Compound VIII is reacted with ethyl chloroformate to obtain a compound of formula IX.

(VIII) + $ClCO_2C_2H_5$ ⟶ 

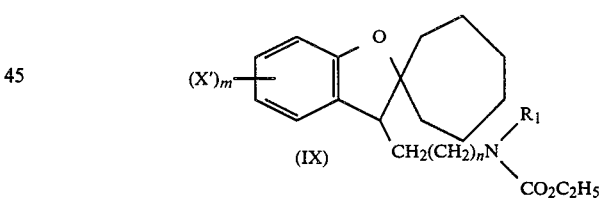

Said reaction is typically conducted in the presence of a basic inorganic salt such as sodium bicarbonate in a suitable medium such as toluene under a reflux condition.

STEP H

Compound IX is hydrolyzed to afford a compound of formula X.

(IX) + $H_2O$ ⟶ 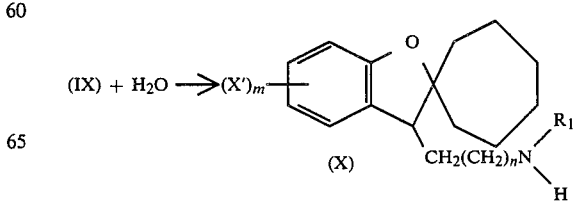

Said hydrolysis is typically conducted in a suitable medium such as a mixture prepared from ethanol and aqueous sodium hydroxide under a reflux condition.

Instead of using STEPS G and H for preparing compound X from compound VIII, one can also use STEPS I and J described below for that purpose.

Compound VIII is reacted with cyanogen bromide to obtain a compound of formula XI.

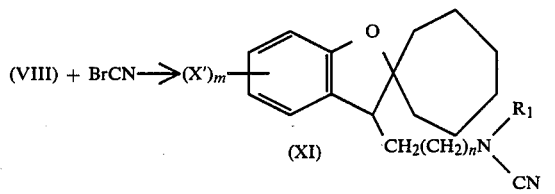

Said reaction is conducted typically in a suitable medium such as dimethylformamide and in the vicinity of room temperature.

STEP J

Compound XI is hydrolyzed to obtain compound X.

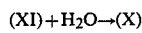

Said hydrolysis can be accomplished, for instance, by adding compound XI to aqueous sulfuric acid of suitable concentration such as about 25 weight % and refluxing the mixture.

STEP K

Compound X is reacted with a methane sulfonyl compound of the formula $CH_3SO_3R_4$ where $R_4$ is loweralkyl, arylloweralkyl or diarylloweralkyl to afford a compound of formula XII.

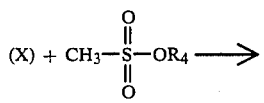

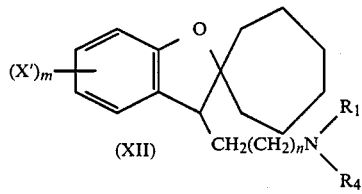

Said reaction is conducted typically in a suitable medium such as a mixture of acetonitrile and water in the presence of an acid scavenger such as potassium carbonate at a temperature of about 50°–80° C.

STEP L

As an alternative to STEP K above, compound X is reacted with a chloride compound of the formula $R_4$—Cl to afford compound XII.

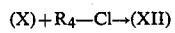

Said reaction is conducted typically in a suitable medium such as a mixture of acetonitrile and water in the presence of an acid scavenger such as potassium carbonate at a temperature of about 50°–80° C.

STEP M

Compound X is reacted with an acyl chloride compound of the formula $R_5$—CO—Cl where $R_5$CO represents a loweralkanoyl, arylloweralkanoyl or diarylloweralkanoyl (except that formyl is excluded in this step), to afford a compound of formula XIII.

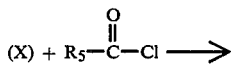

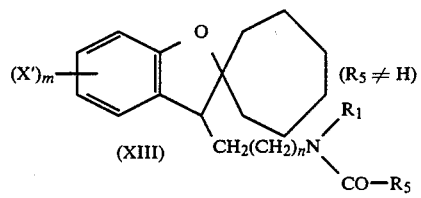

Said reaction is typically conducted in a suitable solvent such as chloroform and in the presence of triethylamine at a temperature of about 20°–50° C.

STEP N

Where $R_5CO$ is a formyl group in formula XIII, the formyl compound of formula XIII-a may be prepared by first preparing acetic-formic anhydride from formic acid and acetic anhydride and reacting it with compound X.

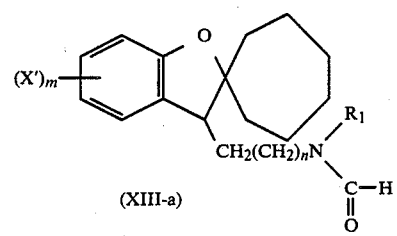

The first step is typically conducted by adding formic acid to acetic anhydride and stirring the mixture at about 50°–60° C. The second step is typically conducted by adding a solution of compound X in a suitable solvent such as tetrahydrofuran to the mixture obtained from the first step at a temperature of about 20°–50° C.

STEP O

Compound XIII ($R_5 \neq H$) is reduced with LiAlH$_4$ to afford the aforementioned compound XII (where $R_4$ is not methyl).

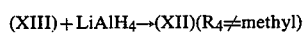

Said reduction is typically conducted in a suitable medium such as anhydrous tetrahydrofuran at a temperature of about 0°–30° C.

STEP P

Compound V is reacted with hydroxylamine to afford an oxime compound of formula XIV.

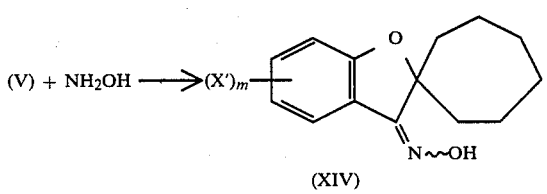

Said reaction is typically conducted in a suitable medium such as a mixture prepared from hydroxylamine hydrochloride, absolute ethanol and pyridine and under a reflux condition.

In this specification and the appended claims, the oxime compound having the —OH group on the same side as the spiroheptane ring is defined as the (E)-isomer; the oxime with the —OH on the same side as the benzene ring is defined as the (Z)-isomer. The same definitions shall also apply to derivatives of the oxime compound where oxime hydrogen is replaced with other groups.

STEP Q

Compound XIV is reacted with a strong base such as sodium hydride to form an oxime anion and the latter is reacted with a halide compound of the formula Hal-CH$_2$(CH$_2$)$_n$NR$_1$R$_3$ where Hal is chlorine, bromine or iodine to afford a compound of formula XV.

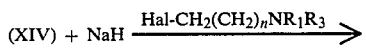

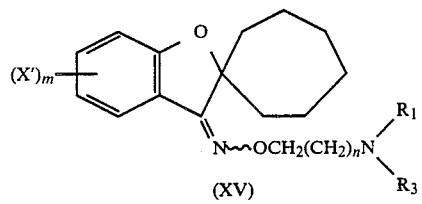

The first step is typically conducted by stirring a mixture comprising compound XIV, sodium hydride and a suitable medium such as anhydrous dimethylformamide at room temperature or a vicinity thereof, whereas the second step is typically conducted by adding ClCH$_2$(CH$_2$)$_n$NR$_1$R$_3$ to the mixture obtained at the end of the first step and stirring the reaction mixture at room temperature or a vicinity thereof.

STEP R

Compound XIV is reacted with a strong base such as sodium hydride to form an oxime anion and the latter is reacted with epibromohydrin to afford a compound of formula XVI.

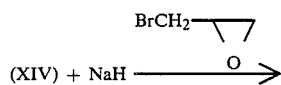

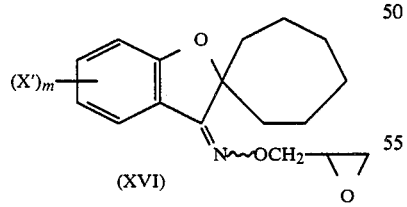

The first and second steps above are conducted in manners similar to the first and second steps, respectively, of STEP Q.

STEP S

Compound XVI is reacted with a compound of the formula HNR$_1$R$_3$ to afford a compound of formula XVII.

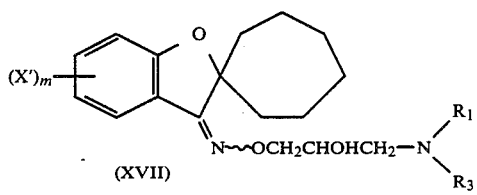

Said reaction is typically conducted in a suitable solvent such as absolute ethanol under a reflux condition.

STEP T

Compound XIV is reduced with sodium borohydride in the presence of nickel (II) chloride to afford a compound of formula XVIII.

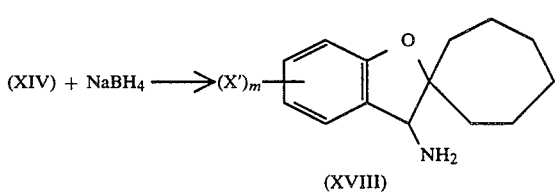

Said reduction is typically conducted in a suitable medium such as methanol or ethanol, or a mixture of both at a temperature between about −15° C. and 10° C.

STEP U

Compound XVIII can be converted to various compounds of formula XIX by utilizing various reaction steps described above. See for instance STEPS G, I, K, L, M, O, and Q above.

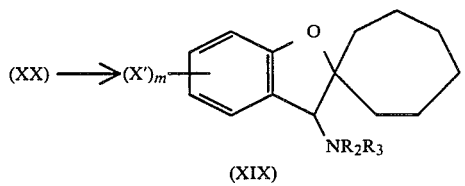

STEP V

Compound V is reduced with sodium borohydride to afford a compound of the formula XX.

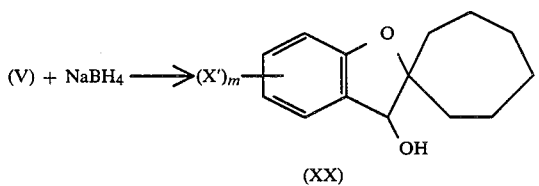

Said reduction is typically conducted in a suitable medium such as ethanol at room temperature or a vicinity thereof.

STEP W

Compound XX can be converted to various compounds of formula XXI by utilizing various reaction steps described above in substantially the same manner as above. In utilizing STEP Q, however, the reaction between compound XX and sodium hydride may be conducted at a higher temperature than room temperature, for instance, about 80°–90° C.

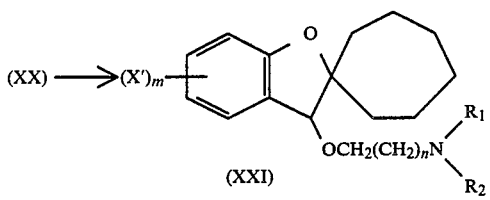

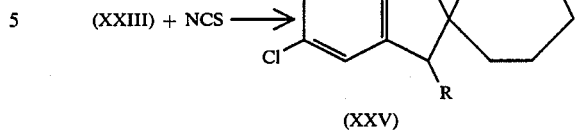

STEP X

As an alternative to the foregoing steps, a compound of formula XXII may be prepared by reacting a compound of formula XXIII with N-bromosuccinimide (NBS).

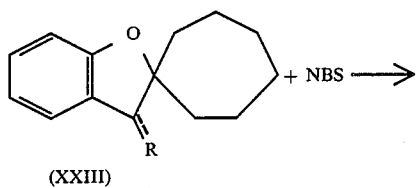

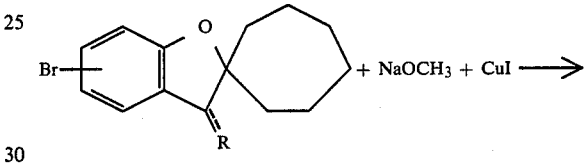

Said bromination is conducted typically in a suitable solvent such as anhydrous methanol in the vicinity of room temperature.

STEP Y

As an alternative to the foregoing steps, a compound of formula XXIV may be prepared by reacting compound XXII with N-bromosuccinimide.

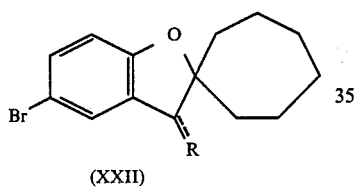

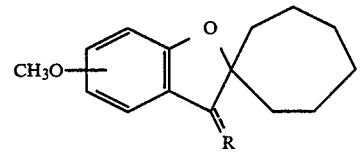

Said bromination is conducted typically in a suitable solvent such as anhydrous methanol in the vicinity of room temperature.

STEP Z

As an alternative to the foregoing steps, a compound of formula XXV may be prepared by reacting compound XXIII with N-chlorosuccinimide (NCS).

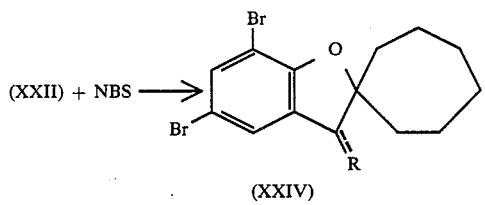

Said chlorination is typically conducted in a suitable solvent such as dimethylformamide in the vicinity of room temperature.

STEP AA

As an alternative to the foregoing steps, the introduction of a methoxy group into the phenyl ring of formula I may be accomplished by reacting a bromo compound shown below with sodium methoxide in the presence of cuprous iodide and a suitable medium such as CH$_3$OH/-dimethylformamide preferably under a reflux condition.

STEP BB

Where a hydroxyl group or groups are to be introduced onto the phenyl ring of compound I of this invention, it is generally preferable to use a method whereby a compound of formula I in which group X is methoxy is chosen and the R-substituent is finalized first according to one or more of the foregoing steps and thereafter the resultant methoxy compound is cleaved in a routine manner known to the art to afford the desired compound. For example, said conversion of methoxy group to hydroxy group can be accomplished by reacting the methoxy compound with pyridine hydrochloride at a temperature of about 200°–220° C.

The spiro[benzofuran-2(3H),1'-cycloheptane]s of formula I of the present invention are useful as antihypertensive agents due to their ability to depress blood pressure in mammals. Antihypertensive activity is measured in the spontaneous hypertensive rat by the indirect tail cuff method described in "Methods in Pharmacology", A. Schwartz, Ed., Vol. I, Appleton-Century Crofts, New York, N. Y., 1971, p. 135. In this procedure a group of five animals are treated orally for three days with the test compound in relation to a control group of the same number. The drop in blood pressure is measured on the third day following administration. The antihypertensive activities of some of the compounds, expressed as a decrease in mean arterial blood pressure (in mm Hg), are given in Table I.

TABLE I
ANTIHYPERTENSIVE ACTIVITY

| Compound | Dose mg/kg p.o. | Blood Pressure Drop mm Hg |
|---|---|---|
| N—Methyl-N—(2-phenylethyl)-spiro[benzofuran-2(3H),1'-cycloheptane]-3-propanamine fumarate | 50 | 76 |
| 3-(3-Dimethylaminopropenyl)-spiro[benzofuran-2(3H),1'-cycloheptane] hydrochloride | 50 | 32 |
| N—4-[Bis(4-fluorophenyl)]-butyl-N—methyl-spiro[benzofuran-2(3H),1'-cycloheptane]-3-propanamine fumarate | 30 | 61 |
| (Prior Art Compound) alpha-Methyldopa | 50 | 40 |

Compounds I of the present invention are useful as anticonvulsant agents. The activity of the compounds is demonstrated in the supramaximal electroshock assay(SES). Groups of male mice (18–30 grams) are used. Drugs are prepared using distilled water and if insoluble, a surfactant is added. Control animals receive vehicle. Drugs are routinely administered intraperitoneally. The dosage volume is 10 ml/kg.

The animal's eyes are placed across the output terminals of an A.C. shocker that delivers 206 volts rms for 300 milliseconds. Electrode paste coats the animal's eyes at the point of contact with the terminals.

A compound is considered to give protection if the mouse does not exhibit extensor tonus. Protection is expressed as normalized percent inhibition relative to vehicle control.

Normalized % inhibition =

$$\frac{\frac{\# Rx \text{ protected}}{\# Rx \text{ tested}} - \frac{\# \text{Control protected}}{\# \text{Control tested}}}{1 - \frac{\# \text{Control protected}}{\# \text{Control tested}}} \times 100$$

A time response is carried out using 6 animals per group. Animals are tested at 30, 60 and 120 minutes postdrug. Additional time periods are tested if indicated by previous tests.

When the peak activity time has been determined, a dose response is initiated, using 10 animals per group at that time period. The $ED_{50}$ and 95% confidence interval are calculated by computerized probit analysis.

Results of the anticonvulsant activities of some of the compounds of this invention are shown in Table 2.

TABLE 2
ANTICONVULSANT ACTIVITY(SES)

| Compound | $ED_{50}$ (mg/kg, i.p.) |
|---|---|
| (Z)-O—Dimethylaminoethyl-spiro[benzofuran-2(3H),1'-cycloheptane]-3-one oxime maleate | 30.2 |
| 3-(3-Dimethylaminopropyl)-spiro[benzofuran-2(3H),1'-cycloheptane] hydrochloride | 30.6 |
| (Prior Art Compound) Chlordiazepoxide | 8.0 |

Compounds I of the present invention are useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med., 95, 729 (1957)]. Table 3 shows a result of the test of the analgesic activities of some of the compounds of this invention.

TABLE 3
ANALGESIC ACTIVITY
(Phenylquinone Writhing)

| Compound | % Inhibition at 20 mg/kg, s.c. |
|---|---|
| N—4-[Bis-(4-fluorophenyl)]-butyl-N—methyl-spiro[benzofuran-2(3H),1'-cycloheptane]-3-propanamine fumarate | 70% |
| N—Methyl-N—[3-[spiro[benzofuran-2(3H),1'-cyclohept-3-yl]]propyl]-benzenemethanamine maleate | 54% |
| 5-Chloro-3-(3-dimethylaminopropyl)-spiro[benzofuran-2(3H),1'-cycloheptane] hydrochloride | 40% |
| (Z)-O—[3-[(1-Methylethyl)amino]-2-hydroxypropyl]-spiro[benzofuran-2(3H),1'-cycloheptan]-3-one oxime maleate | 40% |
| (Prior Art Compound) Propoxyphene | $ED_{50}$ = 3.9 mg/kg,s.c. |

Compounds I of the present invention are useful as antidepressant agents due to their ability to prevent tetrabenazine induced ptosis in mice. The method used is as follows.

Male mice weighing 20 to 30 grams are used in test groups of five subjects. All compounds are dissolved, or suspended with one drop of a non-ionic surfactant in distilled water and administered in volumes of 10 ml/kg of body weight. Tetrabenazine (TBZ) solution is made from methanesulfonate salt and the concentration is adjusted to enable the administration of 40 mg/kg of base by intraperitoneal injection (i.p.).

If the test compound is administered intraperitoneally, TBZ is injected 30 minutes after administration. If the test compound is administered orally (p.o.), TBZ is injected 60 minutes after the administration. A control group received solvent and TBZ by the same route and at the same intervals as the drug groups.

Thirty and sixty minutes after TBZ injection the subjects are placed in individual plastic containers (10/½"×8"×6") and one minute after transfer they are scored for ptosis on the followig scale: eyes closed=4, eyes ¾ closed=3, eyes ½ closed=2, eyes ¼ closed=1, and eyes open=0. The total score for each group of five will therefore be from 0 to 20 and these scores are used as indications of drug activity.

The vehicle-control group score is used as a determinate of the validity of each test. If the control score is less than 17, the results are discarded and the test repeated.

For $ED_{50}$ estimation, four or five doses are administered in order to bracket the estimated value and only vehicle-control scores of 17 to 20 are accepted to assure the accuracy of the $ED_{50}$ estimate.

According to the method described above, (Z)-0-dimethylaminoethyl-spiro[benzofuran-2(3H),1'-cycloheptan]-3-one oxime maleate, for instance showed an $ED_{50}$ value of 72.5 mg/kg, i.p. for inhibition of tetrabenazine-induced ptosis.

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 and 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral multiple dose vials made of glass or plastic.

Examples of the compounds of this invention include:
1-(2-Fluorobenzyl)-1-hydroxycycloheptane;
Spiro[benzofuran-2(3H),1'-cycloheptane];
Spiro[benzofuran-2(3H),1'-cycloheptane]-3-one;
3-(3-Dimethylaminopropyl)-3-hydroxy-spiro[benzofuran-2(3H),1'-cycloheptane];
3-(3-Dimethylaminopropenyl)-spiro[benzofuran-2(3H),1'-cycloheptane]hydrochloride;
3-(3-Dimethylaminopropyl)-spiro[benzofuran-2(3H),1'-cycloheptane]hydrochloride;
N-Methyl-3-[spiro[benzofuran-2(3H),1'-cycloheptan]-3-yl]propyl carbamic acid ethyl ester;
N-Methyl-[3-[spiro(benzofuran-2(3H),1'-cyclohept-3-yl]propyl]cyanamide;
3-(3-Methylaminopropyl)-spiro[benzofuran-2(3H),1'-cycloheptane]hydrochloride;
N-[4-[Bis(3-fluorophenyl)]-butyl]-N-methyl-spiro[benzofuran-2(3H),1'-cycloheptane]-3-propanamine maleate;
N-[4-[Bis(4-fluorophenyl)]-butyl]-N-methyl-spiro[benzofuran-2(3H),1'-cycloheptane]-3-propanamine fumarate;
N-Methyl-N-[3-[spiro[benzofuran-2(3H),1'-cyclohept-3-yl]]propyl]benzamide;
N-Methyl-N-[3-[spiro[benzofuran-2(3H),1'-cyclohept-3-yl]]propyl]benzenemethanamine maleate;
N-Methyl-N-[3-[spiro[benzofuran-2(3H),1'-cyclohept-3-yl]]propyl]phenylacetamide;
N-Methyl-N-(2-phenylethyl)-spiro[benzofuran-2(3H),1'-cycloheptane]-3-propanamine fumarate;
(Z)-Spiro[benzofuran-2(3H),1'-cyclohept]-3-one oxime;
(E)-Spiro[benzofuran-2(3H),1'-cyclohept]-3-one oxime;
(Z)-0-Dimethylaminoethyl-spiro[benzofuran-2(3H),1'-cyclohept]-3-one oxime maleate;
(Z)-0-(Oxiran-2-yl-methyl)spiro[benzofuran-2(3H),1'-cyclohept]-3-one oxime;
(Z)-0-[3-[(1-Methylethyl)amino]-2-hydroxypropyl]-spiro[benzofuran-2(3H),1'-cyclohept]-3-one oxime maleate;
(Z)-0-[3-[(1,1-Dimethylethyl)amino]-2-hydroxypropyl]-spiro[benzofuran-2(3H),1'-cyclohept]-3-one oxime maleate;
3-Amino-spiro[benzofuran-2(3H),1'-cycloheptane]hydrochloride;
N-[Spiro[benzofuran-2(3H),1'-cyclohept-3-yl]]formamide;
N-[4-[Bis(4-fluorophenyl)]-butyl]-N-[spiro[benzofuran-2(3H),1'-cyclohept-3-yl]]formamide;
N-4-[Bis(4-fluorophenyl)]butyl-N-[spiro[benzofuran-2(3H),1'-cyclohept-3-yl]]methanamine maleate;
3-Hydroxy-spiro[benzofuran-2(3H),1'-cycloheptane];
3-(2-Dimethylaminoethoxy)-spiro[benzofuran-2(3H),1'-cycloheptane]hydrochloride;
3-(3-Dimethylaminopropoxy)-spiro[benzofuran-2(3H),1'-cycloheptane]fumarate;
5-Bromo-spiro[benzofuran-2(3H),1'-cycloheptane];
5-Bromo-spiro[benzofuran-2(3H)'1'-cycloheptane]-3-one;
5-Bromo-3-(3-dimethylaminopropyl)-3-hydroxy-spiro[benzofuran-2(3H),1'-cycloheptane];
5-Bromo-3-(3-dimethylaminopropenyl)-spiro[benzofuran-2(3H),1'-cycloheptane]hydrochloride;
5-Bromo-3-(3-dimethylaminopropyl)-spiro[benzofuran-2(3H),1'-cycloheptane]hydrochloride;

5,7-Dibromo-3-(3-dimethylaminopropyl)-spiro[benzofuran-2(3H),1'-cycloheptane]hydrochloride hydrate; and 5-Chloro-3-(3-dimethylaminopropyl)-spiro[benzofuran-2(3H),1'-cycloheptane]hydrochloride.

The following examples are given for illustrative purposes and are not to be considered as limiting the invention disclosed herein. All temperatures are given in degress Celsius.

EXAMPLE 1

1-(2-Fluorobenzyl)-1-hydroxycycloheptane

To a suspension of 16.05 g of magnesium turnings in 200 ml of anhydrous diethyl ether was added a solution of 71.34 ml of o-fluorobenzyl chloride in 250 ml of ether at a rate sufficient to maintain the pot temperature at about 30° C. while cooling the flask in an ice water bath. The reaction was initiated by addition of a few iodine crystals. After the completion of the addition the mixture was stirred under nitrogen at ambient temperature for 45 minutes, and thereafter a solution of 58.9 ml of cycloheptanone in 200 ml of ether was added over a 25 minute period, keeping the pot temperature at about 20° C. with cooling. After the addition the mixture was stirred at ambient temperature for 1 hour and thereafter cooled to 8° C. and treated with 500 ml of saturated ammonium chloride solution (cautiously at first). After 10 minutes of vigorous stirring, the mixture was poured into a separatory funnel, the phases were separated and the aqueous phase was extracted with ether (2×250 ml). The combined ether extracts were washed with 250 ml of saturated ammonium chloride solution, dried over sodium sulfate, filtered and concentrated in vacuo to an oil weighing 109.94 g which crystallized to a solid (mp 35°–40° C.) after removal from high vacuum. A 10 g portion of this material was purified by preparative high performance liquid chromatography (HPLC hereafter) preparative using dichloromethane as a solvent; m.p. 35°–38° C.

ANALYSIS:
Calculated for $C_{14}H_{19}FO$: 75.64% C; 8.61% H.
Found: 75.75% C; 8.61% H.

EXAMPLE 2

Spiro[benzofuran-2(3H),1'-cycloheptane]

To a stirred suspension of 23.32 g of sodium hydride (as a 50% dispersion in mineral oil) in 1.5 liters of benzene (dried over molecular sieves) was rapidly added a solution of 69.9 g of 1-(2-fluorobenzyl)-1-hydroxycycloheptane in 500 ml of benzene. After the addition the mixture was heated to reflux under nitrogen, and 100 ml of dimethylformamide (distilled over BaO) was added to the refluxing mixture. After 118 hours of reflux, the mixture was cooled in ice water and treated with 2.0 liters distilled water. After stirring for a few minutes the phases were separated and the aqueous phase was extracted with hexane (once with 2 liters and twice with one liter). The combined organic extracts were washed with water (1.0 liter) and saturated sodium chloride solution (1.0 liter) and thereafter dried over anhydrous sodium sulfate. Filtration and concentration in vacuo afforded 65.9 g of a crude oil which was given a preliminary purification by preparative HPLC using dichloromethane as solvent. This treatment afforded 28.09 g of product as well as 9.2 g of unreacted starting material. The product was further purified by preparatory HPLC, using hexane/dichloromethane (4:1) as a solvent. This treatment afforded 21.18 g of product as an oil which was 97.6% pure by GC. Vacuum distillation of this material afforded 6.17 g of pure distillate, b.p. 85°–87° C. @ 0.20 mm.

ANALYSIS:
Calculated for $C_{14}H_{18}O$: 83.12% C; 8.97% H.
Found: 83.35% C; 8.95% H.

EXAMPLE 3

Spiro[benzofuran-2(3H),1'-cycloheptane]-3-one

To a stirred mixture of 28.28 g of potassium persulfate, 7.98 g of cupric sulfate and 185 ml of distilled water was rapidly added a solution of 10.58 g of spiro[benzofuran-2(3H),1'-cycloheptane]in 185 ml of acetonitrile. After heating the mixture at reflux for 3 hours, additional 7.07 g of potassium persulfate was added and the reflux was continued for another hour, at which point a GC analysis showed only ketone. The reaction mixture was cooled, diluted with 1.0 liter of distilled water and extracted with ether (once with 1 liter and twice with 500 ml). The combined organic extracts were washed with water (700 ml) and saturated sodium chloride solution (700 ml) and dried overnight over anhydrous sodium sulfate. The extracts were filtered and concentrated in vacuo to an oil weighing 8.94 g. This material was purified by vacuum distillation to yield 7.55 g of distillate. The fraction boiling at 93°–99° C. @ 0.25 mm was submitted for elemental analysis.

ANALYSIS:
Calculated for $C_{14}H_{16}O_2$: 77.57% C. 7.46% H.
Found: 77.86% C; 7.64% H.

EXAMPLE 4

3-(3-Dimethylaminopropyl)-3-hydroxy-spiro[benzofuran-2(3H), 1'-cycloheptane]

A stirred mixture of 0.72 g of magnesium turnings in 10 ml of anhydrous diethyl ether containing a few drops of 1,2-dibromoethane and a crystal of iodine was treated with a solution of 3.65 g of freshly-distilled (b.p. 132° C.) 3-dimethylaminopropyl chloride in 10 ml of ether. After the addition, 20 ml of benzene was added and the mixture refluxed for one hour. At this point a solution of 3.24 g of spiro[benzofuran-2(3H),1'-cycloheptane]3-one was added to the refluxing mixture and the reflux continued under nitrogen for 24 hours, at which point a thin layer chromatography (TLC hereafter) showed no ketone. After the mixture was stirred overnight at room temperature, it was cooled in ice water and treated with 50 ml of saturated ammonium chloride solution while the pot temperature was kept below 20° C. during the addition. After 45 minutes of stirring, the mixture was partitioned between 150 ml of saturated ammonium chloride solution and 100 ml of ether, the phases were separated, and the aqueous phase was extracted with more ether (2×25 ml). The combined organic phases were washed with water (2×100 ml) and saturated sodium chloride solution (50 ml), dried over anhydrous sodium sulfate for 3 hours, filtered and concentrated in vacuo to an oil which began to crystallize. The mixture was triturated to a solid with petroleum ether and the solid filtered to afford 3.24 g of a solid, m.p. 96°–98.5° C. The process was repeated on the filtrate to afford 0.36 g of second crop. Recrystallization from petroleum ether afforded 2.58 g of a crystalline solid, m.p. 97°–99.5° C.

ANALYSIS:
Calculated for $C_{19}H_{29}NO_2$: 75.20% C; 9.63% H; 4.62% N.

Found: 75.32% C; 9.54% H; 4.51% N.

EXAMPLE 5

3-(3-Dimethylaminopropenyl)-spiro[benzofuran-2(3H),1'-cycloheptane]hydrochloride A solution of 8.76 g of 3-(3-dimethylaminopropyl)-3-hydroxy-spiro[benzofuran-2(3H),1'-cycloheptane]in 200 ml of absolute ethanol was treated with 5 ml of concentrated hydrochloric acid at room temperature. The solution (acidic to pH paper) grew warm. After 20 minutes at room temperature, TLC showed not more than a trace of the starting material. The reaction mixture was concentrated in vacuo to a solid. This material was triturated with ether, filtered and dried to afford 8.71 g of a solid, m.p. 226°–228° C. Recrystallization of 4.0 g of this material afforded 3.24 g of a solid, m.p. 227°–229° C.

ANALYSIS:
Calculated for $C_{19}H_{27}NO \cdot HCl$: 70.89% C; 8.77% H; 4.35% N.
Found: 71.36% C; 8.84% H; 4.29% N.

EXAMPLE 6

3-(3-Dimethylaminopropyl)-spiro[benzofuran-2(3H),1'-cycloheptane]hydrochloride A solution of 4.05 g of 3-(3-dimethylaminopropenyl)-spiro[benzofuran-2(3H),1'-cycloheptane]hydrochloride in 175 ml of 95% aqueous ethanol was hydrogenated under 40 psi (pounds per square inch) of hydrogen at room temperature. After shaking the mixture for four hours, the catalyst was filtered off and washed with more ethanol. The filtrate was concentrated in vacuo to a solid. This material was triturated with ether, filtered and dried to afford 3.95 g of a solid, m.p. 195°–198° C. Another batch of material previously prepared in a similar manner was combined with the crude solid, the solids were suspended in 100 ml of boiling ethyl acetate, and acetone was gradually added to the boiling mixture until a solution was obtained (400 ml of hot solution). The boiling solution was filtered and the filtrate allowed to stand at room temperature for 1.5 hours and thereafter cooled in ice water for 2.5 hours. The recrystallized solid was filtered, washed with ethyl acetate and ether, and dried to afford 3.31 g of crystalline solid, m.p. 195°–197° C.

ANALYSIS:
Calculated for $C_{19}H_{29}NO \cdot HCl$: 70.45% C; 9.34% H; 4.33% N.
Found: 70.58% C; 9.45% H; 4.15% N.

EXAMPLE 7

N-Methyl-3-[spiro[benzofuran-2(3H),1'-cycloheptane]-3-yl]propyl carbamic acid ethyl ester To a stirred mixture, kept under nitrogen, of 7.85 g of 3-(3-dimethylaminopropyl)-spiro[benzofuran-2(3H),1'-cycloheptane] and 11.7 g of powdered sodium bicarbonate in 250 ml of toluene was added 5.2 ml of ethyl chloroformate. The mixture was refluxed overnight and thereafter an additional 2.6 ml of ethyl chloroformate was added. The mixture was refluxed for another 5 hours and thereafter stirred overnight at room temperature. Water (250 ml) was then added with stirring. The organic phase was separated and washed successively with 2N-hydrochloric acid, water and brine, dried over anhydrous sodium sulfate and concentrated in vacuo to an oil. This material was used as such for subsequent synthesis. The IR, NMR and Mass Spectra were in accord with the designated structure.

EXAMPLE 8

N-Methyl-[3-[spiro[benzofuran-2(3H),1'-cyclohept-3-yl]propyl]cyanamide

To a stirred solution, under nitrogen, of 11.6 g of 3-(3-dimethylaminopropyl)-spiro[benzofuran-2(3H),1'-cycloheptane]in 140 ml of dimethylsulfoxide was added 4.45 g of cyanogen bromide. The latter dissolved quickly and the reaction temperature rose from 23 to 32° C. After 2 hours, an additional charge of 0.85 g of cyanogen bromide was added and the solution was stirred overnight at room temperature. The reaction fluid was then partitioned between 250 ml of ether and 250 ml of saturated aqueous sodium bicarbonate solution. The two phases were very carefully shaken (gas evolution) and the layers were separated. The aqueous phase was extracted with 250 ml of ether. The ether extracts were then combined, washed with water and with saturated aqueous sodium chloride solution, dried over anhydrous sodium sulfate and concentrated in vacuo to a gum weighing 8.92 g. This material was purified further by flash chromatography on 450 g of silica gel using dichloroethane as eluant to afford 8.23 g of the cyanamide as an oil. This material was used as such for subsequent synthesis. The IR, NMR and Mass Spectra were all in accord with the designated structure.

EXAMPLE 9

3-(3-Methylaminopropyl)-spiro[benzofuran-2(3H),1'-cycloheptane]hydrochloride A solution prepared from 9.53 g of N-methyl-3-[spiro[benzofuran-2(3H),1'-cycloheptan]-3-yl]propyl-carbamic acid ethyl ester, 140 ml of absolute ethanol and 70 ml of 20% aqueous sodium hydroxide solution was refluxed for about 30 hours under nitrogen. Most of the ethanol was removed in vacuo, and the aqueous residue extracted with ether (2×200 ml). The ether extracts were washed with water (100 ml) and extracted with 2N HCl solution (1×100 ml, 1×50 ml). The ether phase was washed with water (100 ml) and the latter was added to the aqueous acidic extracts. The mixture was made basic with 10% aqueous sodium hydroxide solution and extracted with ether (2×250 ml). The ether extracts were washed with water (100 ml) and saturated sodium chloride solution (100 ml), dried over anhydrous sodium sulfate, filtered and concentrated in vacuo to an oil weighing 2.51 g after several hours under high vacuum. This material was combined with another batch of crude free base and dissolved in ether (100 ml), and 20 ml of HCl-saturated ether solution was added dropwise with stirring to produce an acidic liquid phase. After a few minutes of stirring, the crude salt was filtered off, washed and dried to afford 4.39 g of a solid, m.p. 174°–176° C. The crude salt was dissolved in 25 ml of boiling absolute ethanol and the hot solution was filtered by gravity, and thereafter the filtrate was treated dropwise with 25 ml of ether to afford 2.8 g of solid, m.p. 177.5°–179.5° C.

ANALYSIS:
Calculated for $C_{18}H_{27}NO \cdot HCl$: 69.77% C; 9.11% H; 4.52% N.
Found: 69.84% C; 8.91% H; 4.42% N.

EXAMPLE 10

3-(3-Methylaminopropyl)-spiro[benzofuran-2(3H),1'-cycloheptane]hydrochloride

A mixture of 7.16 g of N-methyl-[3-[spiro[benzofuran-2(3H),1'-cyclohept-3-yl]propyl]cyanamide and 50 ml of 25% aqueous sulfuric acid was stirred and refluxed under nitrogen overnight. The mixture was then cooled, poured into 250 ml of water, and made alkaline by the addition of 75 ml of 25% aqueous sodium hydroxide solution. This medium was extracted twice with 250 ml of ether. The combined ether extracts were washed with 100 ml of water and 100 ml of saturated aqueous sodium chloride solution and thereafter dried over anhydrous sodium sulfate. Concentration of the solvent in vacuo left 6.06 g of gum. This material was dissolved in 100 ml of ether and the solution was made acidic by addition of 25 ml of hydrogen chloride-saturated ether solution. Filtration of the resulting salt afforded 6.02 g. Recrystallization of the salt from ethanol provided a pure product, mp 177.5°–179.5° C.

EXAMPLE 11

N-[4-[Bis(3-fluorophenyl)]-butyl]-N-methyl-spiro[benzofuran-2(3H),1'-cycloheptane]-3-propanamine maleate A mixture of 4.05 g of 3-(3-methylaminopropyl)-spiro[benzofuran-2(3H),1'-cycloheptane], 2.23 g of milled anhydrous potassium carbonate, 5.48 g of [4,4-bis(3-fluorophenyl)butyl]mesylate, 25 ml of acetonitrile and 5 ml of distilled water was stirred and heated under nitrogen at 60°–65° C. overnight. The mixture was then cooled to room temperature and partitioned between 250 ml of ether and 100 ml of saturated aqueous potassium carbonate solution. The phases were separated and the aqueous phase was extracted with another 100 ml of ether. The combined ether extracts were washed with distilled water (2×100 ml) and saturated sodium chloride solution (100 ml) and dried overnight over anhydrous sodium sulfate. Filtration and concentration in vacuo afforded a gum which was dissolved in ethyl acetate and flash-chromatographed on 90 g of silica gel using ethyl acetate as a solvent. This procedure afforded 6.63 g of purified free base. This material was dissolved in 100 ml of ether and the solution seeded with crystals of the maleate salt prepared in a test tube and thereafter treated dropwise with stirring with a solution of 1.42 g of maleic acid in 225 ml of ether. After completion of the addition the mixture was stirred for a short period of time and thereafter filtered. The solid was triturated and washed well with ether and dried in vacuo to afford 6.86 g of a solid, m.p. 123°–127° C. with bubbling. Recrystallization of this material from 50 ml of isopropanol afforded 6.23 g of a solid, m.p. 125.5°–128° C. with bubbling.

ANALYSIS:
Calculated for $C_{34}H_{41}F_2NO\cdot C_4H_4O_4$: 72.01% C; 7.16% H; 2.21% N.
Found: 72.16% C; 7.27% H; 2.14% N.

EXAMPLE 12

N-[4-[Bis(4-fluorophenyl)]-butyl]-N-methyl-spiro[benzofuran-2(3H),1'-cycloheptane]-3-propanamine fumarate A mixture of 4.05 g of 3-(3-methylaminopropyl)-spiro[benzofuran-2(3H),1'-cycloheptane], 2.23 g of milled anhydrous potassium carbonate, 4.57 g of 4-chloro-1,1-bis(4-fluorophenyl)butane, 25 ml of acetonitrile and 5 ml of distilled water was stirred and heated at 65°–70° C. under nitrogen for 44 hours. The mixture was allowed to cool to room temperature and was partitioned between 250 ml of ether and 100 ml of saturated potassium carbonate solution. The phases were separated and the aqueous phase was extracted with an additional 100 ml of ether. The combined organic extracts were washed with water (2×100 ml) and saturated sodium chloride solution (100 ml) and dried over sodium sulfate. Filtration and concentration in vacuo afforded an oil which was flash-chromatographed on 90 g of silica gel using ethyl acetate as a solvent. This procedure afforded an oil which was dissolved in 100 ml of ether and treated dropwise with stirring with a solution of 1.62 g of fumaric acid dissolved in a mixture of 50 ml of absolute ethanol and 100 ml of ether. The solvent was removed in vacuo after the addition and the resultant gum stirred with ether in a stoppered flask with seeds of the fumarate salt previously prepared in a test tube. Within a short time the gum solidified. This material was filtered off, washed with ether and dried in vacuo to afford 5.92 g of a solid, m.p. 130°–133° C. with bubbling. Recrystallization of this material from 50 ml of isopropanol afforded 3.7 g of a solid, m.p. 132°–135° C. with bubbling.

ANALYSIS:
Calculated for $C_{34}H_{41}F_2NO\cdot C_4H_4O_4$: 72.01% C; 7.16% H; 2.21% N.
Found: 72.26% C; 7.11% H; 2.63% N.

EXAMPLE 13

N-Methyl-N-[3-[spiro[benzofuran-2(3H),1'-cyclohept-3-yl]]propyl]-benzamide

To a stirred solution, kept under nitrogen, of 5.59 g of 3-(3-methylaminopropyl)-spiro[benzofuran-2(3H),1'-cycloheptane] and 3.1 ml of triethylamine in 150 ml of chloroform was added dropwise a solution of 2.6 ml of benzoylchloride dissolved in 75 ml of chloroform. After stirirng for 4 hours at ambient temperature, 150 ml of water was added. The organic phase was separated, washed with 2N-hydrochloric acid and brine, dried over anhydrous sodium sulfate and concentrated in vacuo. This afforded the benzamide as a gum which was very pure by TLC and used as such for the subsequent synthesis. The IR, NMR and Mass Spectra were in accord with the designated structure.

EXAMPLE 14

N-Methyl-N-[3-[spiro[benzofuran-2(3H),1'-cyclohept-3-yl]]propyl]benzenemethanamine maleate To a suspension of 2.28 g of lithium aluminum hydride in 100 ml of dry tetrahydrofuran was added dropwise under nitrogen over 20 minutes a solution of 7.55 g of N-methyl-N-[3-[spiro[benzofuran-2(3H),1'-cyclohept-3-yl]]propyl]benzamide in 100 ml of tetrahydrofuran. The mixture was cooled in ice-methanol during the addition to keep the pot temperature below 0° C. After removing the bath and stirring the mixture overnight at room temperature, it was again cooled in ice-methanol and treated dropwise with 100 ml of saturated sodium sulfate solution. This mixture was partitioned between 500 ml of water and 500 ml of ether and the phases were separated. The aqueous phase was extracted with another 250 ml of ether and the combined ether extracts were washed with water (2×150 ml) and 150 ml of saturated sodium chloride solution and dried over anhydrous sodium sulfate. Filtration and concentration in vacuo afforded an oil weighing 7.07 g. This material was dissolved in 50 ml of ether and treated dropwise with stirring with a solution of 2.44 g of maleic acid in 250 ml of ether. A slightly gummy solid precipitated first during the early stage of the addition, but a well-formed solid was produced as the addition was continued. After completion of the addition the mixture was swirled and the lighter solid was decanted from the heavier solid as well as possible. The decanted solid was washed with ether and dried to afford 6.74 g of crude maleate salt, m.p. 118°–121° C. Recrystallization twice from isopropanol afforded 4.2 g of crystalline solid, m.p. 121°–123° C.

ANALYSIS:

Calculated for $C_{25}H_{33}NO \cdot C_4H_4O_4$: 72.62% C; 7.78% H; 2.92% N.

Found: 72.77% C; 8.12% H; 2.86% N.

EXAMPLE 15

N-Methyl-N-[3-[spiro[benzofuran-2(3H),1'-cyclohept-3-yl]]propyl]phenylacetamide

To a solution of 6.4 g of 3-(3-methylaminopropyl)-spiro[benzofuran-2(3H),1'-cycloheptane], 170 ml of chloroform and 3.6 ml of triethylamine was added dropwise with stirring under nitrogen over a 1 hour period a solution of 3.4 ml of phenylacetyl chloride in 85 ml of chloroform. After 30 minutes of stirring at ambient temperature, TLC showed complete reaction. The mixture was poured into a separatory funnel and the organic phase was washed with 100 ml of water and 100 ml of saturated sodium chloride solution and dried over anhydrous sodium sulfate. Filtration and concentration in vacuo afforded a gum. This material was purified by flash-chromatography on 250 g of silica gel using ether/hexane (1:1) as a solvent. Fractions containing the purified product were combined and concentrated in vacuo to afford a gum weighing 8.77 g.

ANALYSIS:

Calculated for $C_{26}H_{33}NO_2$: 79.75% C; 8.49% H; 3.58% N.

Found: 79.60% C; 8.51% H; 3.33% N.

EXAMPLE 16

N-Methyl-N-(2-phenylethyl)-spiro[benzofuran-2(3H),1'-cycloheptane]-3-propanamine fumarate To a stirred suspension of 1.71 g of lithium aluminum hydride in 75 ml of dry tetrahydrofuran cooled in an ice/methanol bath was added dropwise under nitrogen over 15 minutes a solution of 5.85 g of N-methyl-N-[3-[spiro[benzofuran-2(3H),1'-cyclohept-3-yl]]propyl]-phenylacetamide in 75 ml of tetrahydrofuran. The bath was removed after completion of the addition and the mixture stirred at ambient temperature. After 2 hours, TLC showed no starting material. The mixture was cooled in ice water and 17 ml of saturated aqueous sodium sulfate solution was added dropwise to consume any unreacted reagent. The mixture was then filtered through a Celite pad. The filtrate was concentrated in vacuo and the residue partitioned between 250 ml of ether and 100 ml of water. The ether phase was washed with 100 ml of saturated sodium chloride solution, dried over anhydrous sodium sulfate, filtered and concentrated in vacuo to an oil weighing 5.15 g. This material was dissolved in 100 ml of ether, seeded with seeds of the fumarate salt previously prepared in a test tube, and treated dropwise with stirring with a solution prepared from 1.74 g of fumaric acid, 100 ml of ether and 50 ml of absolute ethanol. After the completion of the addition the mixture was stirred for a short period of time and thereafter filtered, and the salt was washed with ether and dried to afford 1.0 g of a solid. The filtrate was concentrated in vacuo to a gum, which solidified upon stirring in a stoppered flask with 250 ml of ether. The solid was filtered off, washed with ether, combined with the previous solid and dried to afford 5.05 g of a solid, m.p. 127°–130° C. with bubbling. Purification of this material was as follows. It was dissolved in 25 ml of absolute ethanol, the solution was filtered, the filtrate was allowed to cool to room temperature and 125 ml of ether was added dropwise with stirring. The resultant solid was filtered off, washed with ether and with hexane and dried to afford 0.95 g of a solid, m.p. 172°–174° C. with bubbling, which TLC and spectroscopic analyses indicated to be largely the secondary amine cleavage product. The filtrate was concentrated in vacuo to an oil which crystallized upon dilution with ether. The solid was filtered off, washed with ether and dried to afford 3.13 g of a solid, m.p. 128°–130° C. with bubbling. This material was dissolved in 75 ml of boiling ethyl acetate, the boiling solution was treated with activated charcoal, and the boiling mixture was filtered with mild suction. After standing at room temperature, the filtrate was refrigerated overnight whereupon 2.13 g of solid was obtained in two crops, m.p. 129°–132° C.

ANALYSIS:

Calculated for $C_{26}H_{35}NO \cdot C_4H_4O_4$: 73.00% C; 7.96% H; 2.84% N.

Found: 72.85% C; 7.84% H; 2.79% N.

EXAMPLE 17

Part (1)

(Z)-Spiro[benzofuran-2(3H),1'-cycloheptan]-3-one oxime

A mixture of 10.81 g of spiro[benzofuran-2(3H),1'-cycloheptane]-3-one, 100 ml of absolute ethanol, 34.75 g of hydroxylamine hydrochloride and 100 ml of pyridine was heated at reflux overnight under nitrogen and thereafter cooled to room temperature. The mixture was poured into 500 ml of 2N aqueous hydrochloric acid and extracted with hexane (2×200 ml). The combined hexane extracts were washed with 2N hydrochloric acid (100 ml), distilled water (100 ml) and saturated sodium chloride solution (100 ml). After the last wash, the oxime began to crystallize out of the hexane extracts; dichloromethane was added to redissolve any crystallized solid and the solution was dried overnight over anhydrous sodium sulfate. Filtration and concentration in vacuo afforded a gum which was triturated to solid with hexane. This material was filtered off and recrystallized from 60 ml of boiling hexane to afford 7.28 g of needles, m.p. 98.5°–103.5° C. Recrystallization twice more from 60 ml portions of hexane afforded 5.01 g of pure major (Z) isomer as needles, m.p. 104°–106.5° C.

ANALYSIS:

Calculated for $C_{14}H_{17}NO_2$: 72.70% C; 7.41% H; 6.06% N.

Found: 72.63% C; 7.43% H; 6.07% N.

Part (2)

(E)-Spiro[benzofuran-2(3H),1'-cycloheptan]-3-one oxime

A mixture of 11.08 g of spiro[benzofuran-2(3H),1'-cycloheptane]-3-one, 100 ml of absolute ethanol, 35.44 g of hydroxylamine hydrochloride and 100 ml of pyridine was heated at reflux overnight under nitrogen and thereafter cooled to room temperature, poured into 500 ml of aqueous 2N hydrochloric acid and extracted with hexane (2×200 ml). The hexane extracts were washed with distilled water (100 ml) and concentrated in vacuo to a solid. This material was dissolved in dichloromethane (250 ml). This solution was washed with 100 ml of saturated sodium chloride solution, dried overnight over anhydrous sodium sulfate, filtered and concentrated in vacuo to a gum. This material was dissolved in 60 ml of boiling hexane, gravity filtered, and the filtrate allowed to stand at room temperature for 4 hours. The liquid was then decanted and the solid was triturated with hexane, filtered and dried to afford 5.38 g of crystalline solid enriched in the major (Z) isomer. The decantate and filtrate were combined with isomer material from a previous experiment containing both isomers and concentrated in vacuo to a solid weighing 9.62 g. This material was purified by preparative HPLC, using 2 columns and hexane/ether (4:1) as solvent. The fractions containing the minor (E) isomer were combined and concentrated in vacuo to afford 2.32 g of solid which TLC showed to be largely the minor isomer. This solid was dissolved in 85 ml of boiling hexane, gravity-filtered, and the filtrate allowed to stand at room temperature for 3 hours. The liquid was then decanted and the solid triturated with fresh hexane, filtered and dried to afford the minor (E) isomer as prisms, mp 148.5°–151.5° C.

ANALYSIS:

Calculated for $C_{14}H_{17}NO_2$: 72.70% C; 7.41% H; 6.06% N.

Found: 72.88% C; 7.37% H; 5.80% N.

EXAMPLE 18

(Z)-O-Dimethylaminoethyl-spiro[benzofuran-2(3H),1'-cycloheptan]-3-one oxime maleate To a suspension of 2.64 g of sodium hydride in 175 ml of dry dimethylformamide was added, under nitrogen, a solution of 6.2 g of (Z)-spiro[benzofuran-2(3H),1'-cycloheptan]-3-one oxime in 100 ml of dimethylformamide. After stirring for 15 minutes, 7.72 g of 2-dimethylaminoethyl chloride hydrochloride was added all at once. The addition produced a vigorous gas evolution and a rise in pot temperature to 33° C. After stirring the mixture overnight at room temperature, the mixture was cooled in ice water and treated dropwise with 125 ml of saturated ammonium chloride solution and thereafter partitioned between 500 ml of distilled water and 500 ml of ether. The phases were separated and the aqueous phase was extracted with another 250 ml of ether. The combined ether extracts were washed with 250 ml of saturated sodium chloride solution, dried over anhydrous sodium sulfate, filtered and concentrated in vacuo to an oil weighing 7.92 g. This material was dissolved in 100 ml of ether and treated dropwise with stirring with a solution of 3.35 g of maleic acid in 400 ml of ether. After stirring for a short period of time, the crude salt was filtered off, washed with ether and dried to afford 10.03 g of a solid, m.p. 181.5°–183.5° C. Recrystallization of this material from 275 ml of isopropanol afforded 9.02 g of needles, m.p. 183.5°–186.5° C.

ANALYSIS:

Calculated for $C_{18}H_{26}N_2O_2 \cdot C_4H_4O_4$: 63.14% C; 7.23% H; 6.70% N.

Found: 63.08% C; 7.53% H; 6.65% N.

EXAMPLE 19

(Z)-O-(Oxiran-2-yl-methyl)spiro[benzofuran-2(3H),1'-cycloheptan]-3-one oxime

To a stirred suspension of 1.0 g of sodium hydride in 50 ml of dry dimethylformamide (DMF) kept under nitrogen was added a solution of 2.9 ml of (Z)-spiro[benzofuran-2(3H),1'-cycloheptan]3-one oxime in 100 ml of DMF dropwise over a 15 minute period. After 30 minutes of further stirring, a solution of 2.9 ml of epibromohydrin in 50 ml of DMF was added dropwise over a 5 minute period. After 1 hour at room temperature, the mixture was diluted with 500 ml of water and extracted twice with ether. The combined ether extracts were washed with water and brine, dried over anhydrous sodium sulfate and concentrated in vacuo to give 8.4 g of the desired product as an oil. This material was purified further by flash chromatography on 200 g of silica gel, using hexane/dichloromethane (1:1) as an eluant. This provided 8.29 g of pure product as an oil. This material was used as such for subsequent synthesis. The IR, NMR and Mass Spectra were in accord with the designated structure.

EXAMPLE 20

(Z)-O-[3-[(1-Methylethyl)amino]-2-hydroxypropyl]-spiro[benzofuran-2(3H),1'-cycloheptan]-3-one oxime maleate A mixture of 3.94 g of (Z)-O-(oxiran-2-yl-methyl)-spiro[benzofuran-2(3H),1'-cycloheptan]-3-one oxime, 70 ml of absolute ethanol and 3.5 ml of isopropylamine was stirred and refluxed under nitrogen for 2 hours. The mixture was concentrated in vacuo to a light gum weighing 5.0 g after 2.5 hours under a high vacuum. This material was dissolved in 50 ml of ether and seeded with seeds of the maleate salt prepared in a test tube. A solution of 1.75 g of maleic acid in 150 ml of ether was then added dropwise with stirring. After the addition the solid was filtered off and dried in vacuo to afford 5.45 g of a solid. Recrystallization of this material from 25 ml of absolute ethanol afforded 4.15 g of a crystalline solid, m.p. 155°–157° C.

ANALYSIS:

Calculated for $C_{20}H_{30}N_2O_3 \cdot C_4H_4O_4$: 62.32% C; 7.41% H; 6.06% N.

Found: 62.25% C; 7.39% H; 6.01% N.

EXAMPLE 21

(Z)-O-[3-[(1,1-Dimethylethyl)amino]-2-hydroxypropyl]spiro[benzofuran-2(3H),1'-cycloheptan]-3-one oxime maleate A mixture of 4.02 g of (Z)-O-(oxiran-2-yl-methyl)-spiro[benzofuran-2(3H), 1'-cycloheptan]-3-one oxime, 70 ml of absolute ethanol and 4.4 ml of t-butylamine was stirred and refluxed under nitrogen for 3 hours. The mixture was concentrated in vacuo to a light gum weighing 4.88 g. This material was dissolved in 50 ml of ether and treated dropwise with stirring with a solution of 1.7 g of maleic acid in 150 ml of ether. The precipitated solid was filtered off, washed with ether and dried in vacuo to afford 5.89 g of crude maleate salt as a solid, m.p. 198°–199.5° C. with bubbling. Recrystallization from 100 ml of methanol afforded 4.65 g of a crystalline solid, m.p. 208°–211° C. with bubbling.

ANALYSIS:

Calculated for $C_{21}H_{32}N_2O_3 \cdot C_4H_4O_4$: 63.00% C; 7.61% H; 5.88% N.

Found: 62.90% C; 7.60% H; 5.80% N.

EXAMPLE 22

3-Amino-spiro[benzofuran-2(3H),1'-cycloheptane]hydrochloride

A solution prepared from 6.1 g of an isomeric mixture of (Z)-spiro[benzofuran-2(3H),1'-cycloheptan]-3-one oxime and (E)-spiro[benzofuran-2(3H),1'-cycloheptan]-3-one oxime, 12.55 g of nickel (II) chloride hexahydrate and 100 ml of methanol was cooled in ice-methanol under nitrogen to $-13°$ C. and treated with a solution prepared from 9.99 g of sodium borohydride, 50 ml of methanol and 50 ml of absolute ethanol, dropwise over 20 minutes under nitrogen (maximum temperature $=8°$ C.). The addition funnel was rinsed with additional 10 ml of methanol and the liquid was added to the reaction mixture. After 90 minutes, the mixture was poured into 500 ml of distilled water containing 1.0 liter of crushed ice and made acidic by addition of 250 ml of 2N hydrochloric acid solution. Some unreacted oxime was noted floating atop this mixture, which was left to filter through a Celite pad overnight. The pad was washed with water and the filtrate made basic by addition of an aqueous sodium hydroxide solution. This material was then extracted with ether ($3 \times 250$ ml) and the organic extracts were washed with saturated sodium chloride solution ($3 \times 250$ ml) and thereafter dried overnight over anhydrous sodium sulfate. Filtration and concentration in vacuo afforded an oil, which was dissolved in 100 ml of ether and made acidic by addition of hydrogen chloride - saturated ether solution (10 ml). Filtration, washing with ether and drying in vacuo afforded 2.78 g of a solid, m.p. 244°–249° C. This material was combined with 1.2 g of crude HCl salt prepared in a similar manner and dissolved in 50 ml of absolute ethanol. The solution was filtered hot and the filtrate allowed to stand at room temperature for 3 hours and thereafter cooled in ice water for 1 hour. The recrystalized solid was then filtered off, washed and dried to afford 1.99 g of needles, m.p. 260°–262° C. The filtrate was concentrated in vacuo to afford 1.22 g of a solid which was recrystallized from 15 ml of absolute ethanol to afford another 0.63 g of needles, m.p. 256°–257.5° C. The two crops of recrystallized solid, identical by TLC, were combined and milled with a mortar and pestle to make a uniform mixture. This mixture had m.p. 260°–261° C. and the analytical results shown below.

ANALYSIS:

Calculated for $C_{14}H_{19}NO \cdot HCl$: 66.26% C; 7.94% H; 5.52% N.

Found: 65.98% C; 7.72% H; 5.39% N.

EXAMPLE 23

N-[Spiro[benzofuran-2(3H),1'-cyclohept-3-yl]formamide

A flask containing 8.5 ml of acetic anhydride was cooled under nitrogen in an ice-methanol bath, and 4.2 ml of formic acid was added dropwise with stirring. After the addition the mixture was heated at 50°–61° C. for 2 hours and thereafter allowed to cool. After dilution with 7 ml of tetrahydrofuran, a solution of 7.5 g of 3-amino-spiro[benzofuran-2(3H),1'-cycloheptane] in 14 ml of tetrahydrofuran was added dropwise with stirring over a 15 minute period. This addition produced a rise in temperature from 21 to 45° C. After stirring for approximately 1 hour, precipitation of product began to occur. After 2 hours, the mixture was poured into 500 ml of ice water and extracted with ether ($2 \times 350$ ml). The ether extracts were washed with 100 ml of 10% aqueous sodium hydroxide solution, 100 ml of water and 100 ml of saturated sodium chloride solution, dried over anhydrous sodium sulfate, filtered and concentrated in vacuo to afford a solid. This material was triturated with petroleum ether/ether (2:1), filtered and dried to afford 7.2 g of crystalline solid, m.p. 144°–146° C. Recrystallization of this material from 500 ml of cyclohexane afforded 6.67 g of crystalline solid, m.p. 144°–146° C.

ANALYSIS:

Calculated for $C_{15}H_{19}NO_2$: 73.44% C; 7.81% H; 5.71% N.

Found: 73.82% C; 8.01% H; 5.52% N.

EXAMPLE 24

N-[4-[Bis(4-fluorophenyl)]-butyl]-N-[spiro[benzofuran-2(3H),1'-cyclohept-3-yl]]formamide To a stirred suspension of 1.52 g of sodium hydride in 75 ml of dry dimethylformamide was added dropwise under nitrogen over a 7 minute period a solution of 7.74 g of N-[spiro[benzofuran-2(3H),1'-cyclohept-3-yl]formamide in 75 ml of dimethylformamide. Upon completion of the addition, the mixture was stirred at ambient temperature for 1 hour and thereafter briefly heated to 90° C. After allowing the mixture to cool to 23° C., a solution of 10.64 g of 1-chloro-4-[bis(4-fluorophenyl)]butane in 75 ml of dimethylformamide was added and the mixture stirred overnight at room temperature. After heating at 75°–80° C. for 1 hour the mixture was cooled in ice water and distilled water was added to consume the remaining hydride. The mixture was then partitioned between water (750 ml) and ether (500 ml), the phases were separated, and the aqueous phase was extracted with ether ($2 \times 500$ ml). The combined ether extracts were washed with water (350 ml) and saturated sodium chloride solution (350 ml) and dried over anhydrous sodium sulfate. Filtration and concentration in vacuo afforded a gum weighing 17.48 g. This material was combined with 2.23 g of a material previously prepared in a similar manner and purified by flash chromatography on 440 g of silica gel using dichloromethane as a solvent. The fractions containing the desired product were combined and concentrated in vacuo to a gum which solidified upon trituration with petroleum ether/ether(2:1). The solid was filtered, triturated and washed with hexane to afford 12.05 g of a solid, m.p. 111°–114° C. Recrystallization of this material from 700 ml of hexane afforded 10.27 g of a solid, m.p. 113°–116° C.

ANALYSIS:

Calculated for $C_{31}H_{33}F_2NO_2$: 76.05% C; 6.79% H; 2.86% N.

Found: 75.90% C; 6.71% H; 2.83% N.

EXAMPLE 25

N-[4-[Bis(4-fluorophenyl)]butyl]-N-[spiro[benzofuran-2(3H),1'-cyclohept-3-yl]methanamine To a stirred solution of 7.8 g of N-[4-[bis-(4-fluorophenyl)]butyl]-N-[spiro[benzofuran-2(3H),1'-cyclohept-3-yl]]formamide in 140 ml of dry tetrahydrofuran was added, dropwise at room temperature under nitrogen over a 5-minute period, 40 ml of 1.0 molar borane-methyl sulfide solution in dichloromethane.

After 2 hours at ambient temperature, TLC showed no starting material remaining. The reaction mixture was cooled to 5° C. in an ice water bath, and 40 ml of methanol was added dropwise with stirring. This addition produced vigorous gas evolution. After addition of 100 ml of hydrogen chloride-saturated methanol solution and reflux for one hour, the methanol was removed in vacuo. The residue was made basic with aqueous sodium hydroxide solution and extracted with ether (2×100 ml). The combined ether extracts were washed with 50 ml of water and 50 ml of saturated aqueous sodium chloride solution and dried over anhydrous sodium sulfate. Filtration and concentration of the filtrate in vacuo afforded an oil. 5.79 g of this material was dissolved in 175 ml of ether, the solution was gravity-filtered, and the filtrate was stirred and treated with a solution of 1.3 g of maleic acid in 175 ml of ether. After a short period of stirring, the crude maleate was filtered off, washed with ether and dried to afford 6.23 g of colorless solid, m.p. 145°–147° C. Recrystallization from 50 ml of boiling isopropanol afforded 5.64 g of colorless, crystalline solid, m.p. 144.5°–147° C. with bubbling.

ANALYSIS:

Calculated for $C_{31}H_{35}F_2NO\cdot C_4H_4O_4$: 71.04% C; 6.64% H; 2.37% N.

Found: 70.86% C; 6.76% H; 2.29% N.

EXAMPLE 26

3-Hydroxy-spiro[benzofuran-2(3H),1'-cycloheptane]

A mixture of 7.48 g of spiro[benzofuran-2(3H),1'-cycloheptan]-3-one, 175 ml of denatured ethanol and 1.31 g of sodium borohydride was stirred for 23 hours at room temperature under nitrogen. After addition of 250 ml of distilled water and 10–15 minutes of stirring, the mixture was partitioned between 250 ml of distilled water and 250 ml of ether. The phases were separated and the aqueous phase extracted with additional ether (2×250 ml). The combined organic extracts were washed with distilled water (250 ml) and saturated sodium chloride solution (250 ml) and thereafter dried over anhydrous sodium sulfate. Filtration and concentration in vacuo afforded a solid which was triturated, filtered and washed with hexane. The filtrate was concentrated in vacuo to afford a second crop. Trituration and washing with hexane were repeated to afford in two crops 6.75 g of a crystalline solid, m.p. 104°–107° C.

ANALYSIS:

Calculated for $C_{14}H_{18}O_2$: 77.03% C; 8.31% H.

Found: 77.11% C; 8.39% H.

EXAMPLE 27

3-(2-Dimethylaminoethoxy)-spiro[benzofuran-2(3H),1'-cycloheptane] hydrochloride

To a suspension of 2.08 g of sodium hydride in 50 ml of dry dimethylformamide (DMF) was added under nitrogen a solution of 3.77 g of 3-hydroxy-spiro[benzofuran-2(3H),1'-cycloheptane]in 50 ml of DMF. The mixture was heated to 85° C. under nitrogen to pre-form the alkoxide. After recooling the mixture to room temperature, 7.48 g of 2-dimethylaminoethyl chloride hydrochloride was added and the mixture was stirred overnight at room temperature under nitrogen. The mixture was diluted with water (500 ml) and extracted with ether (2×250 ml). The ether extracts were washed with water (100 ml) and saturated sodium chloride solution (100 ml) and dried over anhydrous sodium sulfate. Filtration and concentration in vacuo afforded an oil weighing 2.64 g. This material was taken up in 100 ml of ether and treated dropwise with stirring with hydrogen chloride-saturated ether until the liquid phase was acidic to a pH paper. The solid was then filtered off, washed with ether and dried to afford 2.41 g of a solid, m.p. 123°–125° C. with bubbling. This material was combined with two other samples of crude salt prepared in a similar manner (6.89 g total), and the free base was regenerated and extracted with ether. The ether extract was dried over sodium sulfate and filtered. Concentration of the filtrate in vacuo afforded 4.89 g of crude free base, which was flash-chromatographed on 120 g of silica gel, using 5% methanol/dichloromethane as a solvent. The fractions containing purified product were combined and concentrated in vacuo to afford an oil. Formation of the crude hydrochloride salt was performed as above, affording 3.72 g of a solid which GC showed to be >99% pure. This material was recrystallized by dissolving it in 25 ml of warm, absolute ethanol, allowing the solution to recool to room temperature, and then filtering it by gravity. The filtrate was slowly diluted, with stirring, with 125 ml of ether and after a short period, the mixture was filtered and the solid washed with ether/ethanol (5:1), then with ether and finally with hexane and dried in vacuo to afford 3.11 g of a solid, m.p. 161°–163.5° C.

ANALYSIS:

Calculated for $C_{18}H_{27}NO_2\cdot HCl$: 66.34% C; 8.66% H; 4.30% N.

Found: 66.04% C; 8.71% H; 4.17% N.

EXAMPLE 28

3-(3-Dimethylaminopropoxy)-spiro[benzofuran-2(3H),1'-cycloheptane] fumarate

A mixture of 10.44 g of 3-hydroxy-spiro[benzofuran-2(3H),1'-cycloheptane], 2.3 g of sodium hydride and 115 ml of dry dimethylformamide (DMF) was stirred under nitrogen and heated to 80° C. to pre-form the alkoxide, then cooled back to room temperature and treated with a solution of 11.63 g of distilled dimethylaminopropyl chloride in 115 ml of DMF. A sustained, mild exotherm was observed. After stirring overnight at room temperature under nitrogen, an additional 5.81 g of dimethylaminopropyl chloride in 115 ml of DMF was added. After 3 hours of further stirring at room temperature, the mixture was worked up by pouring it onto a mixture of 400 ml of crushed ice and 36 ml of concentrated hydrochloric acid, basifying with saturated sodium bicarbonate solution and extracting the product with ether (1×500 ml, 1 x 250 ml). The ether extracts were washed with 250 ml of saturated sodium bicarbonate solution and dried overnight over anhydrous sodium sulfate. Filtration and concentration in vacuo afforded an oil weighing 13.1 g. This material was dissolved in 100 ml of ether and treated with a solution of 3.76 g of maleic acid in 250 ml of ether. The salt of the product separated out as an oil; seeding and scratching caused crystallization to occur. The salt was filtered, washed with ether and dried to afford 12.86 g of a solid, m.p. 82°–90° C. A GC analysis of this material showed it to be 94% product. Another 0.3 g of solid product had precipitated out of the filtrate from the crude salt; the solids were combined, suspended in water, and the free base was regenerated by addition of saturated sodium bicarbonate solution. Extraction with ether afforded 8.58 g of an oil. This material was purified by preparative HPLC, using two columns and 5% methanol/dichloromethane as a solvent. 6.89 g of a purified product was obtained as a mixture of solid and oil. The solid was filtered off, and the material from the filtrate was dissolved in ether and treated with a solution of 2.41 g of fumaric acid in a mixture of ether (200 ml) and ethanol (75 ml). The resultant solution was concentrated in vacuo to an oil. Trituration with 100 ml of ether and seeding caused solidification to occur. The solid was filtered, washed with ether and dried to afford 6.63 g of colorless solid, m.p. 111°–117° C. The crude salt was recrystallized by dissolving it in 30 ml of methanol, filtering, and diluting with ether until just faintly turbid (200 ml of ether). After seeding and stirring for 2 hours at room temperature, the recrystallized solid was filtered, washed with ether and dried to afford 4.16 g of crystalline solid, m.p. 119°–120° C.

ANALYSIS:
Calculated for $C_{19}H_{29}NO_2.C_4H_4O_4$: 65.85% C; 7.93% H; 3.34% N.
Found: 65.88% C; 7.76% H; 3.30% N.

EXAMPLE 29

5-Bromo-spiro[benzofuran-2(3H),1'-cycloheptane]

To a solution of 10.11 g of spiro[benzofuran-2(3H),1'-cycloheptane] in 125 ml of dry methanol was added 9.31 g of N-bromosuccimimide under nitrogen. Most of the solid quickly dissolved, and the pot temperature rose from 22° to 34° C. After one hour at ambient temperature, a gas chromatographic analysis showed complete reaction. The reaction mixture was diluted with water (250 ml) and extracted with hexane (2×250 ml). The hexane extracts were washed with water (100 ml) and saturated sodium chloride solution (100 ml), dried over anhydrous sodium sulfate, filtered and concentrated in vacuo to an oil. This material was vacuum-distilled to afford 4.95 g of distillate, b.p. 109°–128° C. at 0.07 mm. NMR analysis of this material indicated that bromination had occurred para to the oxygen atom. Redistillation through a short-path condenser afforded 2.94 g of distillate, b.p. 123°–127° C. at 0.18 mm.

ANALYSIS:
Calculated for $C_{14}H_{17}BrO$: 59.79% C; 6.10% H.
Found: 60.12% C; 6.18% H.

EXAMPLE 30

5-Bromo-spiro[benzofuran-2(3H),1'-cycloheptan]-3-one

To a stirred mixture of 17.57 g of potassium persulfate, 5.19 g of cupric sulfate and 100 ml of distilled water was added a solution of 9.13 g of 5-bromo-spiro[benzofuran-2(3H),1'-cycloheptane] in 100 ml of acetonitrile. The mixture was stirred and heated to reflux; after 1.5 hours, GC showed only 6% unreacted starting material. Another 3.51 g of potassium persulfate was added and the mixture was refluxed for another hour and thereafter cooled to room temperature. The mixture was diluted with water (1.0 liter) and extracted with ether (1×500 ml, 2×250 ml). The combined ether extracts were washed with water (250 ml) and saturated sodium chloride solution (250 ml), dried overnight over anhydrous sodium sulfate, filtered and concentrated in vacuo to a gum weighing 7.63 g. This material was taken up in 100 ml of hexane and gravity-filtered to remove insoluble material, and the flask, filter paper and insoluble material were rinsed with another 100 ml of hexane. The hexane filtrate was concentrated in vacuo to an oil weighing 5.84 g. Vacuum distillation of this material afforded 2.76 g of viscous distillate, b.p. 135°–140° C. @ 0.15 mm.

ANALYSIS:
Calculated for $C_{14}H_{15}BrO_2$: 56.96% C; 4.78% H.
Found: 57.39% C; 5.20% H.

EXAMPLE 31

5-Bromo-3-(3-dimethylaminopropyl)-3-hydroxy-spiro[benzofuran-2(3H),1'-cycloheptane]

A stirred mixture of 2.72 g of magnesium turnings in 32 ml of diethyl ether containing about 0.5 ml of 1,2-dibromoethane was treated with a solution of 13.62 g of freshly distilled 3-dimethylaminopropyl chloride in 32 ml of ether at a rate sufficient to produce and maintain reflux. After the addition, a solution of 16.53 g of 5-bromo-spiro[benzofuran-2(3H),1'-cycloheptan]-3-one in 65 ml of benzene was added, followed by an additional 32 ml of ether and the mixture was refluxed overnight under nitrogen. After 14.5 hours of reflux, the mixture was cooled in ice water and treated cautiously with 140 ml of saturated aqueous ammonium chloride solution. The mixture was then poured into a separatory funnel, the flask was rinsed with a few hundred ml's of distilled water, and the combined mixture was extracted with ether (2×400 ml). The combined organic extracts were washed with water (250 ml) and saturated sodium chloride solution (250 ml), dried over anhydrous sodium sulfate, filtered and concentrated in vacuo to an oil which crystallized to a solid. This material was triturated with petroleum ether and filtered to afford 8.74 g of crude product. Preparative HPLC purification of this material was performed using two columns and 5% methanol/dichloromethane as a solvent. The purest fractions containing the desired material were combined and concentrated in vacuo to a solid. This material was triturated with hexane, filtered and dried to afford 4.16 g of a solid, m.p. 126°–128° C.

ANALYSIS:
Calculated for $C_{19}H_{28}BrNO_2$: 59.68% C; 7.38% H; 3.66% N.
Found: 59.54% C; 7.19% H; 3.59% N.

EXAMPLE 32

5-Bromo-3-(3-dimethylaminopropenyl)-spiro[benzofuran-2(3H),1'-cycloheptane] hydrochloride A solution of 2.58 g of 5-bromo-3-(3-dimethylaminopropyl)-3-hydroxy-spiro[benzofuran-2(3H),1'-cycloheptane] in 60 ml of absolute ethanol containing 5 ml of concentrated hydrochloric acid was refluxed under nitrogen for 1 hour, at which point TLC showed no starting material. The mixture was concentrated in vacuo to a solid. This material was triturated with ether, filtered and dried to afford 2.45 g of a solid, m.p. 207.5°–212° C. This material was combined with another batch of crude salt previously prepared in a similar manner. Recrystallization twice from absolute ethanol/ether afforded 1.38 g of a solid, m.p. 215°–217.5° C.

ANALYSIS:
Calculated for $C_{19}H_{26}BrNO.HCl$: 56.93% C; 6.79% H; 3.50% N.
Found: 56.66% C; 6.90% H; 3.45% N.

EXAMPLE 33

5-Bromo-3-(3-dimethylaminopropyl)-spiro[benzofuran-2(3H),1'-cycloheptane] hydrochloride To a stirred solution of 3.89 g of 3-(3-dimethylaminopropyl)-spiro[benzofuran-2(3H),1'-cycloheptane] hydrochloride in 35 ml of methanol at room temperature under nitrogen was added 2.24 g of N-bromosuccinimide. All solid dissolved rapidly as the pot temperature rose to 33° C. A TLC analysis after 20 minutes showed a complete reaction. The mixture was poured into water (175 ml), and 250 ml of saturated sodium bicarbonate solution was added with stirring. The mixture was then extracted with ether (2×250 ml). The combined organic extracts were washed with water (100 ml) and saturated sodium chloride solution (100 ml), dried briefly over anhydrous sodium sulfate, filtered and concentrated in vacuo to an oil. This material was dissolved in 100 ml of ether and the solution was stirred and treated with hydrogen chloride-saturated ether solution until the liquid phase was acidic to a pH paper. After a few minutes, the salt was filtered off, washed with ether and dried to afford 4.52 g of a solid, m.p. 169°–172° C. This crude salt was combined with two other batches of previously prepared crude salt and recrystallized by dissolving the solids in 20 ml of absolute ethanol, filtering by gravity, and treating the stirred filtrate dropwise with ether (140 ml). After stirring for 30 minutes the recrystallized salt was filtered, triturated and washed with ethanol/ether (1:7) solution, then ether and finally hexane. Drying in vacuo afforded 5.08 g of crystalline solid, m.p. 174°–176° C.

ANALYSIS:

Calculated for $C_{19}H_{28}BrNO.HCl$: 56.65% C; 7.26% H; 3.48% N.

Found: 56.62% C; 7.20% H; 3.38% N.

EXAMPLE 34

5,7-Dibromo-3-(3-dimethylaminopropyl)-spiro[benzofuran-2(3H),1'-cycloheptane] hydrochloride hydrate To a stirred solution of 8.4 g of 5-bromo-3-(3-dimethylaminopropyl)-spiro[benzofuran-2(3H),1'-cycloheptane] hydrochloride in 57 ml of methanol, at room temperature under nitrogen, was added 7.44 g of N-bromosuccinimide. All solid dissolved as the pot temperature rose to 37° C. After stirring overnight at room temperature under nitrogen, the mixture was poured into 250 ml of water, made basic by addition of 100 ml of 10% aqueous sodium hydroxide solution, and extracted with ethyl acetate (2×250 ml). The combined organic extracts were washed with water (100 ml) and saturated sodium chloride solution (100 ml) and dried overnight over anhydrous sodium sulfate. Filtration and concentration in vacuo afforded a mixture of oil and solid. This material was taken up in 100 ml of ethyl acetate and gravity-filtered, and the filtrate was stirred and treated dropwise with 10 ml of hydrogen chloride-saturated ether solution. The precipitated salt was filtered off, washed with ether and dried in vacuo to afford 2.85 g of a solid, m.p. sinters 200°, 202°–204° C. A second crop which had precipitated out of the filtrate was filtered off and washed with ether to afford, without drying, an additional 1.2 g of a solid, m.p. sinters 200°, 201°–202.5° C. The two crops of crude salt were combined and dissolved in 50 ml of absolute ethanol and gravity-filtered, and the filtrate was treated dropwise with ether (350 ml) with stirring. After stirring the mixture for a short period of time, the recrystallized solid was filtered off, washed with ether and dried to afford 2.2 g of a solid, m.p. 203.5°–206° C.

ANALYSIS:

Calculated for $C_{19}H_{27}Br_2NO.HCl.H_2O$: 45.66% C; 6.06% H; 2.80% N.

Found: 45.58% C; 5.96% H; 2.69% N.

EXAMPLE 35

5-Chloro-3-(3-dimethylaminopropyl)-spiro[benzofuran-2(3H),1'-cycloheptane] hydrochloride A mixture of 8.1 g of 3-(3-dimethylaminopropyl)-spiro[benzofuran-2(3H),1'-cycloheptane] hydrochloride, 70 ml of dimethylformamide and 3.34 g of N-chlorosuccinimide was stirred overnight at room temperature under nitrogen. As the reaction proceeded all solid dissolved. After stirring overnight, the mixture was poured into 500 ml of distilled water, made basic by addition of 50 ml of 25% aqueous sodium hydroxide solution and extracted with ether (3×200 ml). The combined ether extracts were washed with 100 ml of water and 100 ml of saturated sodium chloride solution and dried overnight over anhydrous sodium sulfate. Filtration and concentration of the filtrate in vacuo afforded an oil weighing 7.87 g. This material was dissolved in 100 ml of ether and the hydrochloride salt was prepared by dropwise addition of 10 ml of hydrogen chloride-saturated ether solution. The precipitated solid was filtered off, washed with ether and dried to afford 8.23 g of a solid. This material was taken up in 250 ml of distilled water and the free base was liberated by addition of an aqueous sodium hydroxide solution. After extraction with ether (2×100 ml), the combined ether extracts were washed with 10% aqueous sodium hydroxide solution (2×50 ml), water (2×50 ml) and finally saturated sodium chloride solution (50 ml) and dried overnight over anhydrous sodium sulfate. Filtration and concentration in vacuo afforded an oil from which the hydrochloride salt was prepared as above. The crude salt weighed 7.75 g. Recrystallization twice from absolute ethanol/ether afforded 3.28 g of a solid, m.p. 167°–169° C.

ANALYSIS:

Calculated for $C_{19}H_{28}ClNO.HCl$: 63.68% C; 8.16% H; 3.91% N.

Found: 63.36% C; 8.06% H; 3.81% N.

We claim:

1. A compound of the formula

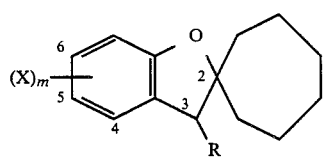

wherein each X is independently H, halogen, loweralkyl, loweralkoxy or OH; m is 1 or 2; and R is —H, =O,

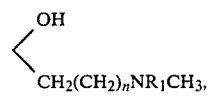

=CH(CH$_2$)$_n$NR$_1$CH$_3$, —CH$_2$(CH$_2$)$_n$NR$_1$R$_2$, =N—OH, =N—OCH$_2$(CH$_2$)$_n$NR$_1$R$_3$,

=N—OCH$_2$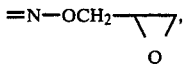

=N-OCH$_2$CHOHCH$_2$NR$_1$R$_3$, —NR$_2$R$_3$, —OH or —OCH$_2$(CH$_2$)$_n$NR$_1$R$_2$, n being 1 or 2, R$_1$ being loweralkyl, R$_2$ being H, loweralkyl, loweralkanoyl, aryllloweralkyl, arylloweralkanoyl, diarylloweralkyl, diarylloweralkanoyl, —CO$_2$C$_2$H$_5$ or —CN and R$_3$ being H, loweralkyl, arylloweralkyl or diarylloweralkyl or a pharmaceutically acceptably acceptable acid addition salt thereof, the term aryl in each occurrence signifying a phenyl group having 0, 1, 2 or 3 substituents each of which being independently loweralkyl, loweralkoxy, halogen or CF$_3$.

2. The compound as defined in claim 1, where R is =CH(CH$_2$)$_n$NR$_1$CH$_3$.

3. The compound as defined in claim 1, where R is =N-O(CH$_2$)$_n$NR$_1$R$_3$.

4. The compound as defined in claim 1, where R is =N-OCH$_2$CHOHCH$_2$NR$_1$R$_3$.

5. The compound as defined in claim 1 where R is NR$_2$R$_3$.

6. The compound as defined in claim 1 where R is CH$_2$(CH$_2$)$_n$NR$_1$R$_2$.

7. The compound as defined in claim 6 where R$_2$ is arylloweralkyl or diarylloweralkyl.

8. The compound as defined in claim 7 where R$_2$ is arylloweralkyl.

9. The compound as defined in claim 8 where R$_1$ is CH$_3$, n is 2, and X is hydrogen or halogen.

10. The compound as defined in claim 1, which is spiro[benzofuran-2(3H),1'-cycloheptane].

11. The compound as defined in claim 1, which is spiro[benzofuran-2(3H),1'-cycloheptane]-3-one.

12. The compound as defined in claim 1, which is 3-(3-dimethylaminopropyl)-3-hydroxy-spiro[benzofuran-2(3H),1'-cycloheptane].

13. The compound as defined in claim 1, which is 3-(3-dimethylaminopropenyl)-spiro[benzofuran-2(3H),1'-cycloheptane].

14. The compound as defined in claim 1, which is 3-(3-methylaminopropyl)-spiro[benzofuran-2(3H),1'-cycloheptane].

15. The compound as defined in claim 1, which is 3-(3-dimethylaminopropyl)-spiro[benzofuran-2(3H),1'-cycloheptane].

16. The compound as defined in claim 1, which is N-methyl-3-[spiro[benzofuran-2(3H),1'-cycloheptan-3-yl]propyl carbamic acid ethyl ester.

17. The compound as defined in claim 1, which is N-methyl-[3-[spiro[benzofuran-2(3H),1'-cyclohept-3-yl]propyl]cyanamide.

18. The compound as defined in claim 1, which is N-methyl-N-[3-[spiro[benzofuran-2(3H),1'-cyclohept-3-yl]]propyl]benzenemethanamine.

19. The compound as defined in claim 1, which is N-methyl-N-(2-phenylethyl)-spiro[benzofuran-2(3H),1'-cycloheptane]-3-propanamine.

20. The compound as defined in claim 1, which is N-[4-[bis(3-fluorophenyl)]-butyl]-N-methyl-spiro[benzofuran-2(3H),1'-cycloheptane]-3-propanamine.

21. The compound as defined in claim 1, which is N-[4-[bis(4-fluorophenyl)]-butyl]-N-methyl-spiro[benzofuran-2(3H),1'-cycloheptane]-3-propanamine.

22. The compound as defined in claim 1, which is N-methyl-N-[3-[spiro[benzofuran-2(3H),1'-cyclohept-3-yl]]propyl]benzamide.

23. The compound as defined in claim 1, which is N-methyl-N-[3-spiro[benzofuran-2(3H),1'-cyclohept-3-yl]]propyl]phenylacetamide.

24. The compound as defined in claim 1, which is (Z) or (E)-spiro[benzofuran-2(3H),1'-cycloheptan]-3-one oxime.

25. The compound as defined in claim 1, which is (Z) or (E)-O-dimethylaminoethyl-spiro[benzofuran-2(3H),1'-cycloheptan]-3-one oxime.

26. The compound as defined in claim 1, which is (Z) or (E)-O-(oxiran-2-yl-methyl)spiro[benzofuran-2(3H),1'-cycloheptan]-3-one oxime.

27. The compound as defined in claim 1, which is (Z) or (E)-O-[3-[(1-methylethyl)amino]-2-hydroxypropyl]-spiro[benzofuran-2(3H),1'-cycloheptan]-3-one oxime.

28. The compound as defined in claim 1, which is (Z) or (E)-O-[3-[(1,1-dimethylethyl)amino]-2-hydroxypropyl]spiro[benzofuran-2(3H),1'-cycloheptan]-3-one oxime.

29. The compound as defined in claim 1, which is 3-amino-spiro[benzofuran-2(3H),1'-cycloheptane].

30. The compound as defined in claim 1, which is N-[spiro[benzofuran-2(3H),1'-cyclohept-3-yl]formamide.

31. The compound as defined in claim 1, which is N-[4-[bis(4-fluorophenyl)]-butyl]-N-[spiro[benzofuran-2(3H),1'-cyclohept-3-yl]]formamide.

32. The compound as defined in claim 1, which is N-[4-[bis(4-fluorophenyl)]butyl]-N-[spiro[benzofuran-2(3H),1'-cyclohept-3-yl]]methanamine.

33. The compound as defined in claim 1, which is 3-hydroxyspiro[benzofuran-2(3H),1'-cycloheptane].

34. The compound as defined in claim 1, which is 3-(2-dimethylaminoethoxy)-spiro[benzofuran-2(3H),1'-cycloheptane].

35. The compound as defined in claim 1, which is 3-(3-dimethylaminopropoxy)-spiro[benzofuran-2(3H),1'-cycloheptane].

36. The compound as defined in claim 1, which is 5-bromospiro[benzofuran-2(3H),1'-cycloheptane].

37. The compound as defined in claim 1, which is 5-bromospiro[benzofuran-2(3H),1'-cycloheptane]-3-one.

38. The compound as defined in claim 1, which is 5-bromo-3-(3-dimethylaminopropyl)-3-hydroxy-spiro[benzofuran-2(3H),1'-cycloheptane].

39. The compound as defined in claim 1, which is 5-bromo-3-(3-dimethylaminopropenyl)-spiro[benzofuran-2(3H),1'-cycloheptane].

40. The compound as defined in claim 1, which is 5-bromo-3-(3-dimethylaminopropyl)-spiro[benzofuran-2(3H),1'-cycloheptane].

41. The compound as defined in claim 1, which is 5-chloro-3-(3-dimethylaminopropyl)spiro[benzofuran-2(3H),1'-cycloheptane].

42. The compound as defined in claim 1, which is 5,7-dibromo-3-(3-dimethylaminopropyl)spiro[benzofuran-2(3H),1'-cycloheptane].

43. An antihypertensive composition comprising an effective blood pressure lowering amount of the compound as defined in claim 1 and a pharmaceutically acceptable carrier therefor.

44. An anticonvulsant composition comprising an effective convulsion preventive amount of the compound as defined in claim 1 and a pharmaceutically acceptable carrier therefor.

45. An analgesic composition comprising an effective pain alleviating amount of the compound as defined in claim 1 and a pharmaceutically acceptable carrier therefor.

46. An antidepressant composition comprising an effective depression alleviating amount of the compound as defined in claim 1 and a pharmaceutically acceptable carrier therefor.

47. A method of treating a patient in need of relief from high blood pressure which comprises administering to the patient an effective amount of the compound as defined in claim 1.

48. A method of treating a patient in need of prevention of convulsion which comprises administering to the patient an effective amount of the compound as defined in claim 1.

49. A method of treating a patient in need of relief from pain which comprises administering to the patient an effective amount of the compound as defined in claim 1.

50. A method of treating a patient in need of relief from depression which comprises administering to the patient an effective amount of the compound as defined in claim 1.

* * * * *

UNITED STATES PATENT AND TRADEMARK OFFICE
CERTIFICATE OF CORRECTION

PATENT NO. : 4,623,657

DATED : November 18, 1986

INVENTOR(S) : Edward J. Glamkowski and Frederick J. Ehrgott, Jr.

It is certified that error appears in the above-identified patent and that said Letters Patent is hereby corrected as shown below:

Column 32, line 50:

In Claim 1: The chemical structure appearing on line 2 should appear as shown below:

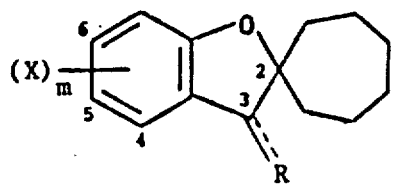

Signed and Sealed this

Tenth Day of March, 1987

Attest:

DONALD J. QUIGG

Attesting Officer

Commissioner of Patents and Trademarks